United States Patent
Wang et al.

[11] Patent Number: 5,858,838
[45] Date of Patent: Jan. 12, 1999

[54] METHOD FOR INCREASING DRAM CAPACITANCE VIA USE OF A ROUGHENED SURFACE BOTTOM CAPACITOR PLATE

[75] Inventors: Chen-Jong Wang; Chia-Shiung Tsai, both of Hsin-Chu, Taiwan

[73] Assignee: Taiwan Semiconductor Manufacturing Company, Ltd., Hsin-Chu, Taiwan

[21] Appl. No.: 27,755

[22] Filed: Feb. 23, 1998

[51] Int. Cl.[6] .............................................. H01L 24/8242
[52] U.S. Cl. ...................... 438/255; 438/398; 438/502; 438/581; 438/630
[58] Field of Search ................... 438/239, 244, 438/253, 254, 255, 387, 396, 397, 398, 502, 509, 581, 582, 583, 630, 682, 964

[56] References Cited

U.S. PATENT DOCUMENTS

| | | | |
|---|---|---|---|
| 4,663,191 | 5/1987 | Choi et al. | 438/682 |
| 5,110,752 | 5/1992 | Lu | 438/255 |
| 5,182,232 | 1/1993 | Chhabra et al. | 438/255 |
| 5,266,514 | 11/1993 | Tuan et al. | 437/52 |
| 5,427,974 | 6/1995 | Lur et al. | 437/60 |
| 5,583,070 | 12/1996 | Liao et al. | 437/52 |
| 5,622,888 | 4/1997 | Sekine et al. | 438/398 |
| 5,634,974 | 6/1997 | Weimer et al. | 117/103 |
| 5,661,068 | 8/1997 | Hirao et al. | 438/398 |
| 5,665,625 | 9/1997 | Sandhu et al. | 438/396 |
| 5,716,883 | 2/1998 | Tseng | 438/253 |
| 5,723,373 | 3/1998 | Chang et al. | 438/253 |
| 5,726,085 | 3/1998 | Crenshaw et al. | 438/255 |
| 5,741,734 | 4/1998 | Lee | 438/398 |
| 5,760,434 | 6/1998 | Zahurak et al. | 438/396 |

*Primary Examiner*—Charles Bowers
*Assistant Examiner*—Jack Chen
*Attorney, Agent, or Firm*—George O. Saile; Stephen B. Ackerman

[57] ABSTRACT

A method for increasing the surface area of a polysilicon storage node electrode, used as a component for a DRAM stacked capacitor structure, has been developed. The method features forming a metal silicide layer, on the top surface of the polysilicon storage node electrode, locally consuming regions of underlying polysilicon during the metal silicide formation. Removal of the metal silicide layer, from the surface of the polysilicon storage node electrode, results in a roughened surface, comprised of crevices in the top surface of the polysilicon storage node electrode, in regions in which localized metal silicide formation had occurred. The crevices in the top surface of the polysilicon storage node electrode result in surface area increases, when compared to counterparts fabricated using smooth polysilicon surfaces.

18 Claims, 4 Drawing Sheets

5,858,838

METHOD FOR INCREASING DRAM CAPACITANCE VIA USE OF A ROUGHENED SURFACE BOTTOM CAPACITOR PLATE

BACKGROUND OF THE INVENTION

1. Field of the Invention

The present invention relate to a method used to fabricate semiconductor devices, and more specifically to a method used to fabricate a dynamic random access memory, (DRAM), device, using a storage node structure, with a roughened top surface.

2. Description of Prior Art

The semiconductor industry is continually striving to improve the performance of semiconductor devices, while still maintaining, or even decreasing the manufacturing cost of these same semiconductor devices. The advent of micro-miniaturization, or the ability to fabricate semiconductor devices, with sub-micron features, has allowed the industry's performance and cost objectives to be successfully addressed. The use of sub-micron features result in decreases in performance degrading capacitances and resistances, thus allowing improved device performance to be realized. In addition the use of micro-miniaturization allows smaller chips, still containing circuit densities comparable to circuit densities obtained with larger semiconductor chips, to be fabricated. This in turn results in an increase in the amount of semiconductor chips obtained from a specific size starting substrate, thus resulting in a reduction of manufacturing cost of a specific chip.

Dynamic random access memory, (DRAM), devices, are being fabricated using a stacked capacitor, (STC), structure, overlying a transfer gate transistor. The shrinking of device features has resulted in a decrease in STC dimensions. Therefore the capacitance of the STC structure, influenced by the dimensions of the storage node electrode, has to be increased via other means. The use of thinner capacitor dielectric layers, or higher dielectric constant materials, used to increase STC capacitance, is limited by process complexity or yield concerns. Therefore the DRAM community has focused on capacitance increases via the creation of storage node electrodes, exhibiting a roughened topology, or a top surface comprised of concave and convex features. The use of a storage node electrode, with a roughened top surface topology, results in an increase in surface area, when compared to counterparts fabricated with a smooth top surface topology, thus resulting in an increase in STC capacitance.

One method of creating a storage node electrode, with a roughened surface, is the formation of an overlying hemispherical grained silicon, (HSG), layer. The ability to create the HSG layer, comprised of silicon bumps, results in surface area increases. Prior art, such as Weimer, et al, in U.S. Pat. No. 5,634,974, describes a method for formation of an HSG silicon layer, to be used as the top layer for a storage node structure. However the method chosen by Weimer, et al, is complex in regards to initially forming silicon seeds, followed by critical annealing procedures. This invention will describe an alternative to HSG silicon, for providing increased surface area for a storage node electrode, resulting in the improved STC capacitance needed for high density DRAM devices. This invention will describe the formation of, and the removal of, a metal silicide layer, from the surface of a storage node electrode, resulting in a roughened, or creviced surface, of polysilicon storage node electrode, resulting in increased surface area, without using HSG silicon layers.

SUMMARY OF THE INVENTION

It is an object of this invention to fabricate a stacked capacitor, (STC) ,structure, of a DRAM device, in which the capacitance of the STC structure, is increased via use of a storage node electrode, exhibiting a roughened top surface.

It is another object of this invention to form a metal silicide layer, on the top surface of a polysilicon storage node electrode, via reaction of an overlying metal layer with regions of the underlying polysilicon storage node electrode.

It is still another object of this invention to remove the metal silicide layer from the underlying polysilicon storage node electrode, resulting in crevices in the surface of underlying polysilicon storage node electrode, in regions in which the metal silicide resided.

In accordance with the present invention a method is described for increasing the surface area of a polysilicon storage node electrode, by forming, and removing, a metal silicide layer, from the top surface of the polysilicon storage node electrode. An insulator layer is deposited on an underlying transfer gate transistor, followed by the creation of a storage node opening, in the insulator layer, exposing a source and drain region of the transfer gate transistor. A polysilicon layer is deposited, and patterned to create a polysilicon storage node electrode, in the storage node opening. A metal layer is next deposited, and subjected to a first anneal procedure, converting the metal, on the polysilicon storage node electrode, to a first metal silicide layer, while leaving the metal layer, on the top surface of the insulator layer, unreacted. After removal of the unreacted metal layer, a second anneal procedure is used to form a second metal silicide layer, consuming regions of the underlying polysilicon storage node electrode. The second metal silicide layer is next removed, resulting in crevices in the underlying polysilicon storage node electrode, in regions in which polysilicon was consumed during the second anneal procedure. The formation of a capacitor dielectric layer, on the creviced, or roughened surface of the polysilicon storage node electrode, is next performed, followed by the creation of a polysilicon upper capacitor plate, resulting in a stacked capacitor structure, featuring a polysilicon storage node electrode with increased surface area as a result of the roughened, top surface.

BRIEF DESCRIPTION OF THE DRAWINGS

The object and other advantages of this invention are best described in the preferred embodiment with reference to the attached drawings that include.

DESCRIPTION OF THE PREFERRED EMBODIMENTS

The method for forming a DRAM device, with a stacked capacitor structure, featuring a polysilicon storage node electrode with a roughened top surface, created to increase surface area, and capacitance, of the stacked capacitor structure, will now be described in detail. The DRAM device, in this invention, will be described as an N channel device, however the process for forming a roughened top surface, polysilicon storage node electrode, can also be applied to DRAM devices, comprised of P channel, transfer gate transistor.

Figure 1:
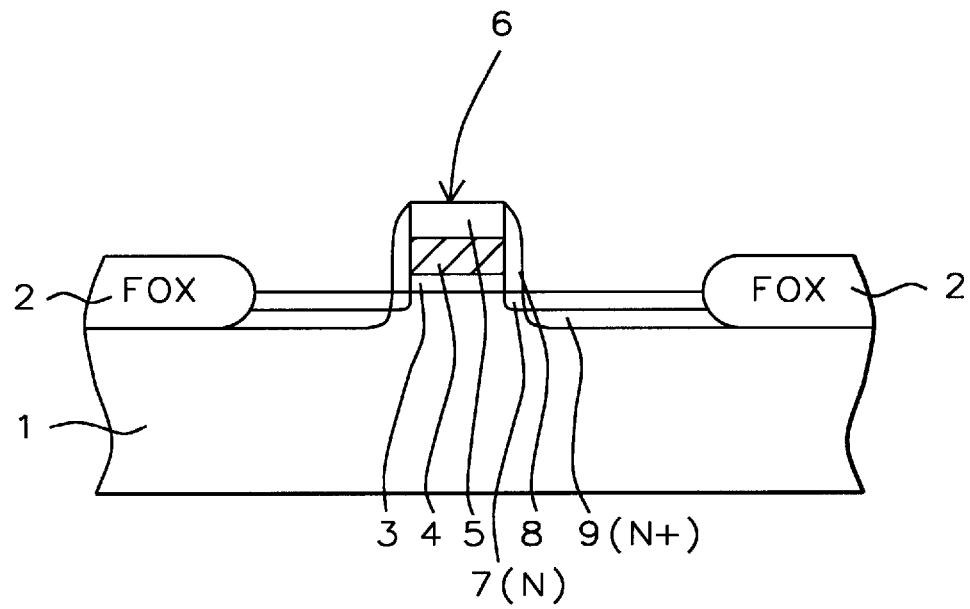
FIGS. 1–8, which schematically, in cross-sectional style, show key stages of fabrication, used to create a storage node electrode with a roughened top surface.

Referring to FIG. 1, a P type, semiconductor substrate 1, with a <100>, single crystalline orientation, is used. Field oxide, (FOX), regions 2, are used for purposes of isolation. Briefly the FOX regions 2, are formed via thermal oxidation, in an oxygen-steam ambient, at a temperature between about 850° to 1050° C., to a thickness between about 3000 to 5000 Angstroms. A patterned oxidation resistant mask of silicon nitride-silicon oxide is used to prevent FOX regions 2, from growing on areas of semiconductor substrate 1, to be used for subsequent device regions. After the growth of the FOX regions 2, the oxidation resistant mask is removed via use of a hot phosphoric acid solution for the overlying, silicon nitride layer, and a buffered hydrofluoric acid solution for the underlying silicon oxide layer. After a series of wet cleans, a gate insulator layer 3, of silicon dioxide is thermally grown in an oxygen-steam ambient, at a temperature between about 850° to 1050° C., to a thickness between about 50 to 200 Angstroms. A polysilicon layer 4, is next deposited using low pressure chemical vapor deposition, (LPCVD), procedures, at a temperature between about 500° to 700° C., to a thickness between about 1000 to 3000 Angstroms. The polysilicon can either be grown intrinsically and doped via ion implantation of arsenic or phosphorous, or polysilicon layer 4, can be grown using in situ doping procedures, via the incorporation of either arsine, or phosphine, to the silane ambient. A first insulator layer 5, comprised of silicon oxide, or silicon nitride, is next deposited using LPCVD, or plasma enhanced chemical vapor deposition, (PECVD), procedures, to a thickness between about 2000 to 3000 Angstroms. Conventional photolithographic and reactive ion etching, (RIE), procedures, using $CHF_3$ as an etchant for first insulator layer 5, and using $Cl_2$ as an etchant for polysilicon layer 4, are used to create polysilicon gate structure 6, comprised of first insulator layer 5, and polysilicon layer 4, shown schematically in FIG. 1. Photoresist removal is accomplished via plasma oxygen ashing and careful wet cleans.

A lightly doped source and drain region 7, is next formed via ion implantation of phosphorous, at an energy between about 20 to 50 KeV, at a dose between about 1E13 to 1E14 atoms/cm$^2$. A second insulator layer, comprised of silicon oxide, or silicon nitride, is deposited using either LPCVD or PECVD procedures, at a temperature between about 400° to 700° C., to a thickness between about 800 to 2000 Angstroms, followed by an anisotropic RIE procedure, using $SF_6$ as an etchant, creating insulator spacers, 8, on the sides of polysilicon gate structures 6. A heavily doped source and drain region 9, is then formed via ion implantation of arsenic, at an energy between about 30 to 100 KeV, at a dose between about 1E14 to 5E16 atoms/cm$^2$. This is schematically shown in FIG. 1.

Figure 2:
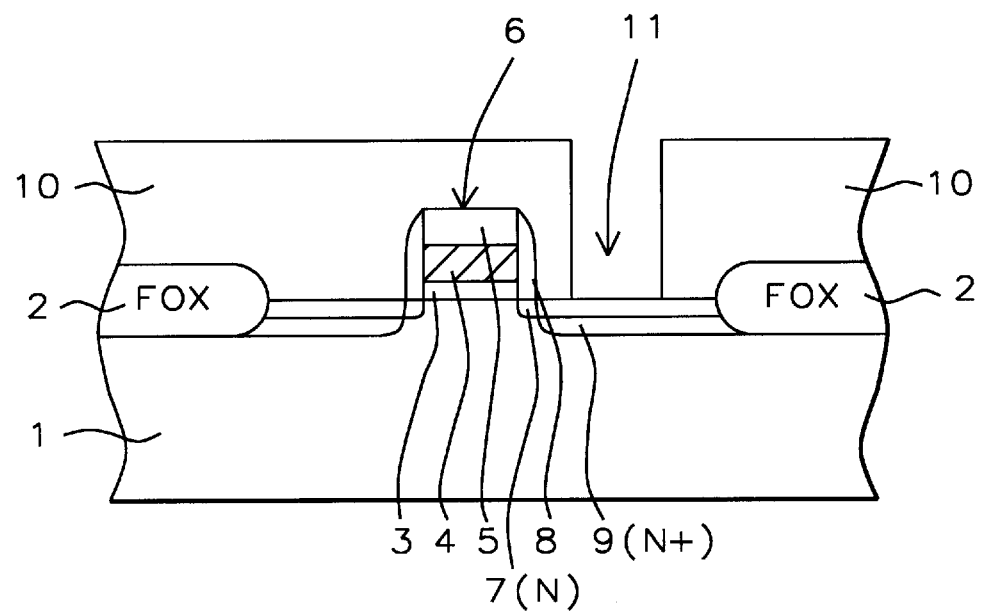

A third insulator layer 10, of silicon oxide, is next deposited using LPCVD or PECVD procedures, at a temperature between about 400° to 800° C., to a thickness between about 3000 to 7000 Angstroms, followed by a planarization procedure, using a chemical mechanical polishing, (CMP), procedure, used to create a smooth top surface for insulator layer 10. Conventional photolithographic and anisotropic RIE procedures, using $CHF_3$ as an etchant for insulator layer 10, are used to create storage node opening 11, in insulator layer 10, exposing the top surface of heavily doped source and drain regions 9. This is schematically shown in FIG. 2. Removal of photoresist shape, used as a mask for the creation of storage node opening 11, is accomplished via use of plasma oxygen ashing and careful wet cleans.

Figure 3:
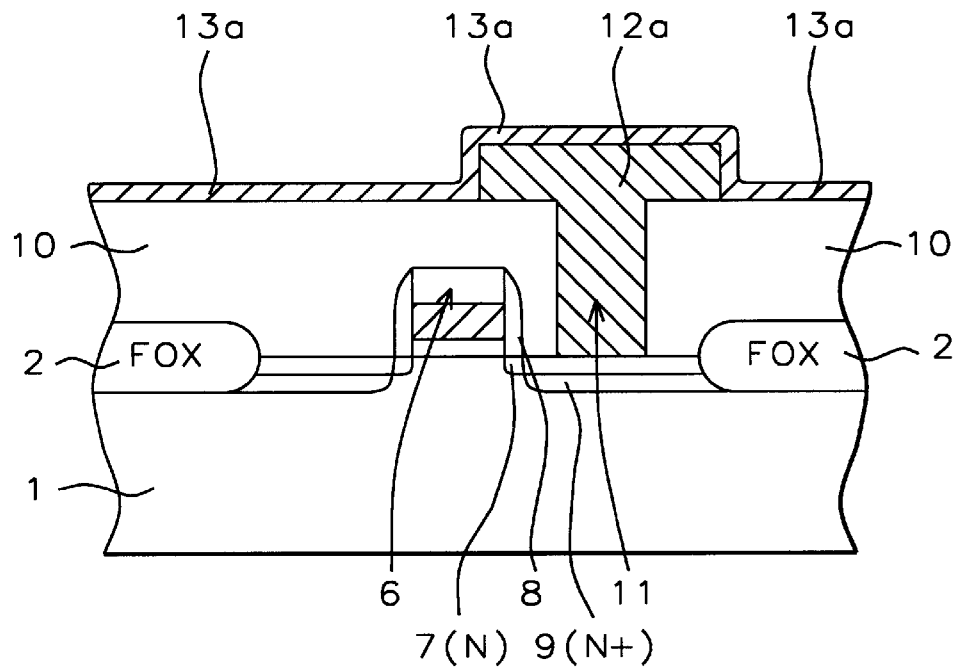

A polysilicon layer is next deposited using LPCVD procedures, to a thickness between about 2000 to 5000 Angstroms, and doped in situ, during deposition, via the addition of arsine, of phosphine, to a silane ambient. Photolithographic and anisotropic RIE procedures, using $Cl_2$ as an etchant, are used to form polysilicon storage node electrode 12a, in storage node opening 11, schematically shown in FIG. 3. After removal of the photoresist shape, used for polysilicon storage node electrode formation, via plasma oxygen ashing and careful wet cleans, a titanium layer 13a, is deposited using R. F. sputtering, to a thickness between about 200 to 400 Angstroms. This is schematically shown in FIG. 3.

Figure 4:
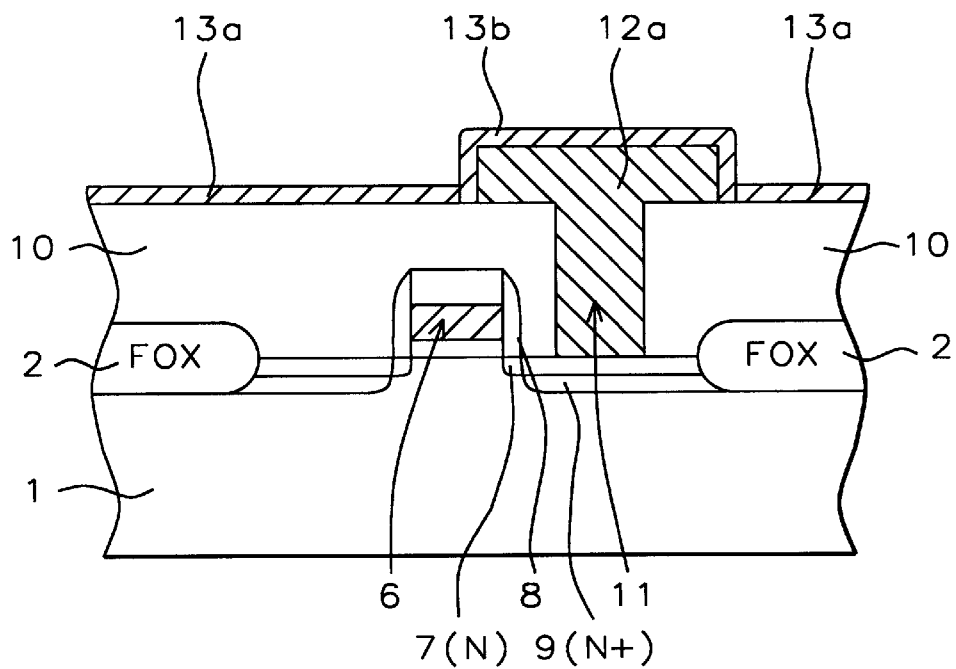
Figure 5:
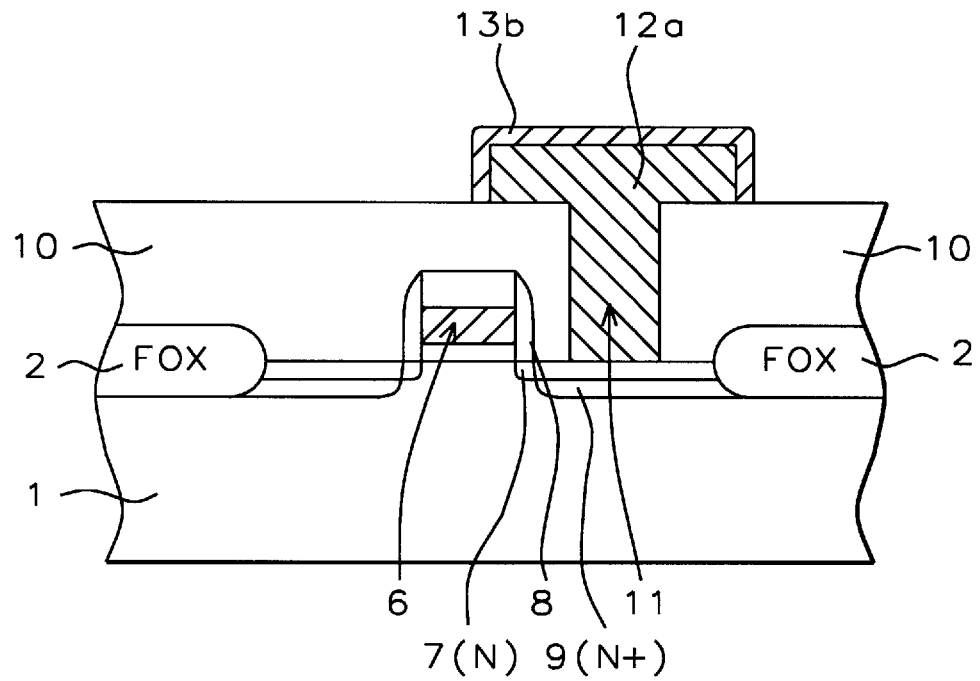

A first rapid thermal anneal, (RTA), procedure is employed, to convert titanium layer 13a, overlying polysilicon storage node electrode 12a, to a first titanium silicide layer 13b, while leaving titanium layer 13a, overlying insulator layer 10, unreacted. This is schematically shown in FIG. 4. The first RTA procedure is performed at a temperature between about 700° to 740° C., for a time between about 20 to 40 sec., in a nitrogen ambient. The purpose of the first RTA procedure is to create a titanium silicide layer that will not be removed during the subsequent removal of unreacted titanium. The level of consumption of polysilicon from the top surface of polysilicon storage node electrode 12a, is still not great enough to create the desired roughened topology of the polysilicon storage node electrode. Removal of unreacted titanium layer 13a, is accomplished using $NH_4OH$ and $H_2O_2$. The result of titanium layer removal is schematically shown in FIG. 5.

Figure 6:
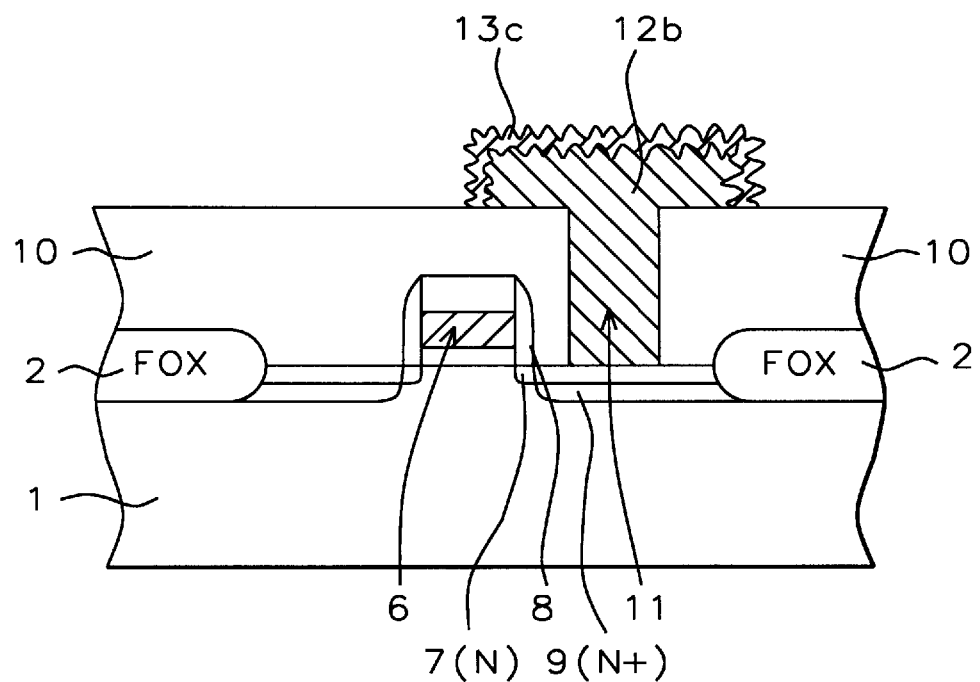

A second RTA procedure is next performed at a temperature between about 860° to 900° C., for a time between about 20 to 40 sec., in a nitrogen ambient, converting first titanium silicide layer 13b, to second titanium silicide layer 13c. The formation of second titanium silicide layer 13c, results in consumption of underlying polysilicon, from the top surface of polysilicon storage node 12a, creating polysilicon storage node electrode 12b, which features a roughened top surface. This is shown schematically in FIG. 6.

Figure 7:
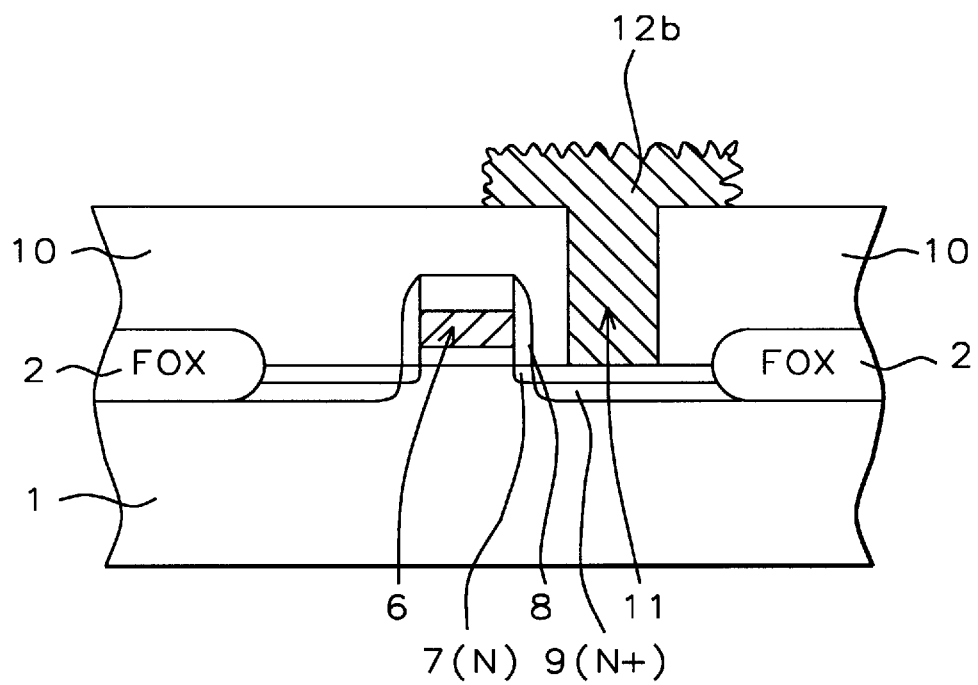

Removal of second titanium silicide layer 13c, is next addressed via either a hydrofluoric acid dip, or via a dry etch procedure, using $SF_6$ and $Cl_2$ as an etchant, with both the wet and dry procedures selectively removing second titanium silicide layer 13c, from the top surface of polysilicon storage node 12b. The removal of second titanium silicide layer 13c, results in crevices in the top surface of polysilicon storage node electrode 12b, with dimensions of between about 0.03 to 0.05 uM in depth, and between about 0.04 to 0.06 uM in width. The crevices in the top surface of polysilicon storage node 12b, were formed via localized reaction of polysilicon and titanium, during the RTA anneals, followed by the removal of second titanium silicide layer 13c. This is schematically displayed in FIG. 7.

Figure 8:
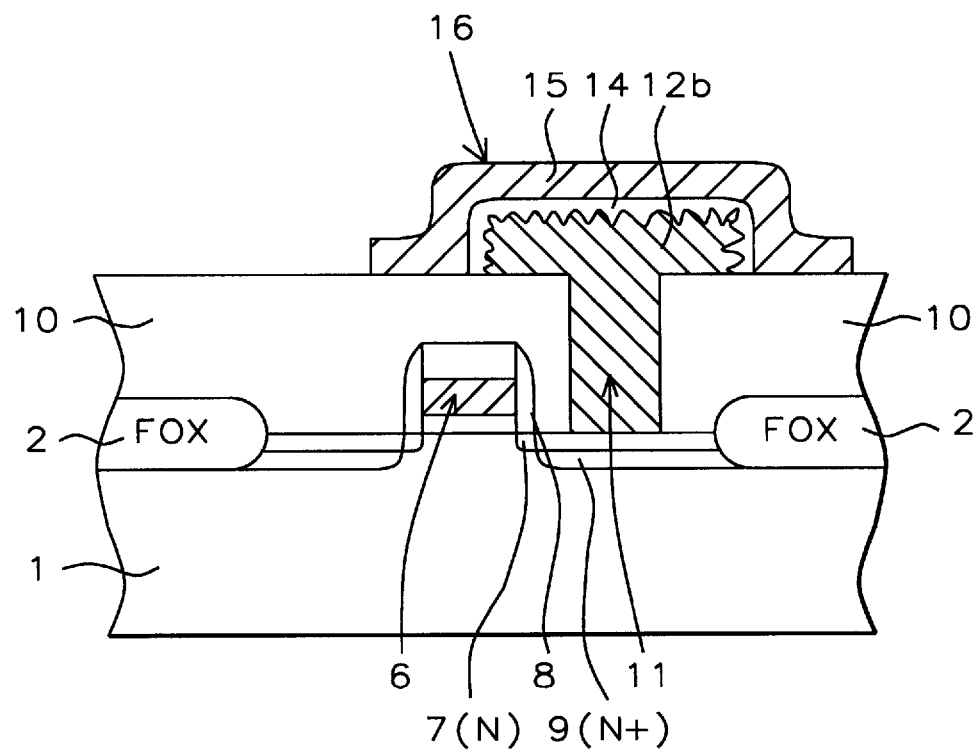

FIG. 8, schematically shows the completion of an STC structure 16, comprised of a storage node electrode 12b, featuring a roughened top surface topology. A capacitor dielectric layer 14, comprised of a composite dielectric layer of silicon oxynitride—silicon nitride—silicon oxide, (ONO), at an equivalent silicon oxide thickness of between about 50 to 80 Angstroms, is formed on the roughened surface of storage node electrode 12b. The ONO layer is created by initially creating a native, silicon oxide layer, between about 10 to 20 Angstroms in thickness, on the surface of polysilicon storage node electrode 12b. A thin layer of silicon nitride is next deposited, using LPCVD procedures, to a thickness between about 40 to 80 Angstroms. An oxidation procedure, performed in an oxygen—steam ambient, is next used to convert the surface of the silicon nitride layer, to a silicon oxynitride layer, thus creating the ONO layer. After creation of capacitor dielectric layer 14, another polysilicon layer is deposited, via LPCVD procedures, to a thickness between about 500 to 2000 Angstroms. The polysilicon layer can be grown using in situ doping techniques, or grown intrinsically and doped via ion implantation procedures, using arsenic or phosphorous. Conventional photolithographic and RIE procedure, using $Cl_2$ as an etchant are used to create upper electrode, or capacitor plate 15, shown schematically in FIG. 8. Photoresist removal is once again performed, using plasma oxygen ashing and careful wet cleans, resulting in STC structure 16, featuring increased capacitor surface area, and thus increased capacitance, resulting from the use of a storage node electrode, comprised of a roughened top surface, achieved via formation and removal of a metal silicide layer.

While this invention has been particularly shown and described with reference to the preferred embodiments thereof, it will be understood by those skilled in the art that various changes in form and details may be made without departing from the spirit and scope of the invention.

What is claimed is:

1. A method of fabricating a stacked capacitor structure for a DRAM device, featuring increased surface area of a storage node electrode, resulting from the removal of a twice annealed, metal silicide layer, from the surface of said storage node electrode, comprising the steps of:

providing a transfer gate transistor, on a semiconductor substrate, comprised of a polysilicon gate structure, on a gate insulator layer, with source and drain regions in said semiconductor substrate, in regions of said semiconductor substrate, not covered by said polysilicon gate structure;

forming a storage node contact opening, in an insulator layer, exposing said source and drain region;

forming a polysilicon storage node electrode, in said storage node contact opening;

depositing a metal layer on the polysilicon storage node electrode and the insulator layer;

performing a first anneal procedure to form a first metal silicide layer, on the surface of said polysilicon storage node electrode, while leaving regions of said metal layer, on top surface of said insulator layer, unreacted;

removing regions of unreacted metal layer, from the top surface of said insulator layer, while leaving said first metal silicide layer on the surface of said polysilicon storage node electrode;

performing a second anneal procedure, to convert said first metal silicide layer to a second metal silicide layer, consuming regions of the top surface of said polysilicon storage node electrode, resulting in a roughened top surface for said polysilicon storage node electrode, directly underlying said second metal silicide layer;

selectively removing said second metal silicide layer from the roughened top surface of said polysilicon storage node electrode;

forming a capacitor dielectric layer on the roughened top surface of said polysilicon storage node electrode; and forming a capacitor plate electrode, on said capacitor dielectric layer.

2. The method of claim 1, wherein said insulator layer is silicon oxide, deposited using LPCVD or PECVD procedures, to a thickness between about 3000 to 7000 Angstroms.

3. The method of claim 1, wherein said storage node contact opening is formed in said insulator layer, via an anisotropic RIE procedure, using $CHF_3$ as an etchant.

4. The method of claim 1, wherein said polysilicon storage node electrode is formed from a polysilicon layer, which is deposited using LPCVD procedures, to a thickness between about 2000 to 5000 Angstroms, and doped in situ, via the addition of arsine or phosphine, to a silane ambient.

5. The method of claim 1, wherein said polysilicon storage node electrode is formed via patterning of a polysilicon layer, using an anisotropic RIE procedure, using $Cl_2$ as an etchant.

6. The method of claim 1, wherein said first metal silicide layer, is a first titanium silicide layer, formed on said polysilicon storage node electrode via deposition of a titanium layer, via R. F. sputtering, to a thickness between about 200 to 400 Angstroms, and followed by a first rapid thermal anneal procedure, performed at a temperature between about 700° to 740° C., for a time between about 20 to 40 sec.

7. The method of claim 1, wherein said second metal silicide layer is a second titanium silicide layer, formed using a second rapid thermal anneal procedure, performed at a temperature between about 860° to 900° C., for a time between about 20 to 40 sec., converting said first metal silicide layer to said second metal silicide layer.

8. The method of claim 1, wherein said second metal silicide layer is removed from the top surface of said polysilicon storage node electrode using a hydrofluoric acid procedure.

9. The method of claim 1, wherein said second metal silicide layer is removed from the top surface of said polysilicon storage node electrode via a selective dry etching procedure, using $SF_6$ and $Cl_2$ as an etchant.

10. The method of claim 1, wherein said roughened top surface, of said polysilicon storage node electrode, is comprised of crevices in the top surface of said polysilicon storage node electrode, between about 0.03 to 0.05 uM in depth, and between about 0.04 to 0.06 uM in width.

11. A method for fabricating a stacked capacitor structure, for a DRAM device, on a semiconductor substrate, wherein the surface area of the stacked capacitor structure, is increased by creating crevices in the top surface of a polysilicon storage node electrode, via selective dry etching removal, of a twice annealed, titanium silicide layer, from the top surface of said polysilicon storage node electrode, comprising the steps of:

providing a transfer gate transistor, comprised of a polysilicon gate structure, on an underlying gate insulator layer, and with source and drain regions in said semiconductor substrate, in a region of said semiconductor substrate, not covered by said polysilicon gate structure;

depositing an insulator layer on the substrate and the transfer gate transistor;

forming a storage node opening in said insulator layer, exposing the top surface of said source and drain region;

depositing an in situ doped polysilicon layer, completely filling said storage node opening;

patterning of said in situ doped polysilicon layer, to form said polysilicon storage node electrode, in said storage node opening;

depositing a titanium layer on the polysilicon storage node electrode and the insulator layer;

performing a first anneal procedure, to selectively form a first titanium silicide layer, on said polysilicon storage node electrode, while said titanium, on the top surface of said insulator layer remains unreacted, removing said titanium layer from the top surface of said insulator layer;

performing a second anneal procedure, converting said first titanium silicide layer, to a second titanium silicide layer, and consuming regions of the top surface of said polysilicon storage node electrode, during said second anneal procedure, and resulting in a roughened top surface for said polysilicon storage node electrode, underlying said second titanium silicide layer, comprised of crevices in the top surface of said polysilicon storage node electrode;

performing a dry etching procedure, using $SF_6$ and $Cl_2$ as etchants, to selectively remove said second titanium silicide layer from said roughened top surface of said polysilicon storage node electrode;

forming a capacitor dielectric layer on said roughened top surface of said polysilicon storage node electrode;

depositing a polysilicon layer on the capacitor dielectric layer; and patterning of said polysilicon layer to form a capacitor plate for said stacked capacitor structure.

12. The method of claim 11, wherein said in situ doped, polysilicon layer, is deposited using LPCVD procedures, to a thickness between about 2000 to 5000 Angstroms, and in situ doped via the addition of arsine or phosphine, to a silane ambient.

13. The method of claim 11, wherein said titanium layer is deposited using R. F. sputtering procedures, to a thickness between about 200 to 400 Angstroms.

14. The method of claim 11, wherein said first anneal procedure, used to from said first titanium silicide layer, is a first rapid thermal anneal procedure, performed at a temperature between about 700° to 740° C., for a time between about 20 to 40 sec.

15. The method of claim 11, wherein said titanium layer, is removed from the top surface of said insulator layer, using $NH_4OH$ and $H_2O_2$.

16. The method of claim 11, wherein said second anneal procedure, used to convert said first titanium silicide layer to said second titanium silicide layer, is a second rapid thermal anneal procedure, performed at a temperature between about 860° to 900° C. for a time between about 20 to 40 sec.

17. The method of claim 11, wherein said crevices, in the roughened top surface of said polysilicon storage node electrode, are between about 0.03 to 0.05 uM in depth, and between about 0.04 to 0.06 uM in width.

18. The method of claim 11, wherein said capacitor dielectric layer is a ONO layer, composed of silicon oxynitride—silicon nitride—silicon oxide, obtained via: the growth of a native oxide on the top surface of said polysilicon storage node electrode, at a thickness between about 10 to 20 Angstroms; LPCVD deposition of a silicon nitride layer, to a thickness between about 40 to 80 Angstroms; and an oxidation to convert the top portion of said silicon nitride layer, to a silicon oxynitride layer.

* * * * *